United States Patent [19]

Lewis et al.

[11] 4,136,182
[45] Jan. 23, 1979

[54] TRIAZOLOPYRIDAZINES USED TO ALLEVIATE BRONCHIAL SPASMS

[75] Inventors: Jon Lewis, Indianapolis; Philip J. Shea, Carmel, both of Ind.

[73] Assignee: The Dow Chemical Company, Midland, Mich.

[21] Appl. No.: 877,061

[22] Filed: Feb. 13, 1978

Related U.S. Application Data

[63] Continuation-in-part of Ser. No. 690,326, May 26, 1976, abandoned, which is a continuation of Ser. No. 569,417, Apr. 18, 1975, abandoned, which is a continuation of Ser. No. 399,566, Sep. 21, 1973, abandoned.

[51] Int. Cl.$^2$ .................. A61K 27/00; A61K 31/495
[52] U.S. Cl. ........................ 424/248.54; 424/248.56; 424/250
[58] Field of Search ............... 424/248.54, 248.56, 424/250

[56] References Cited

U.S. PATENT DOCUMENTS

| 3,079,392 | 2/1963 | Pesson | 260/250 A |
| 3,096,329 | 7/1963 | Steck | 260/250 A |
| 3,483,193 | 12/1969 | Gall et al. | 260/250 AH |
| 3,708,484 | 1/1973 | Anderson et al. | 260/250 A |

FOREIGN PATENT DOCUMENTS

1248409  11/1960  France.

OTHER PUBLICATIONS

Davis et al., Nature, New Biology (1971), vol. 234, No. 45.
Yorugi et al., Takeda Kenkyusho Ha, 32(2), pp. 111–117 (1973).
Chemical Abstracts 67:21884q (1967).
Baso et al., J. Chem. Soc. (Dec. 1963), 8660–8664.
Chemical Abstracts 56:10160b (1962).

Primary Examiner—Leonard Schenkman

[57] ABSTRACT

This invention relates to a method useful for combatting bronchial spasm in mammals by means of administering to mammals a 3,6,8-substituted triazolopyridazine compound such as 8-methyl-6-morpholino-s-triazolo-[4,3-b]pyridazine, 3,8-dimethyl-6-piperidino-s-triazolo-[4,3-b]pyridazine or a pharmacologically-acceptable salt thereof.

7 Claims, No Drawings

TRIAZOLOPYRIDAZINES USED TO ALLEVIATE BRONCHIAL SPASMS

CROSS REFERENCE TO RELATED APPLICATIONS

This is a continuation-in-part of our application Ser. No. 690,326, filed May 26, 1976 now abandoned; which was a continuation of application Ser. No. 569,417, filed Apr. 18, 1975, now abandoned, which was a continuation of application Ser. No. 399,566, filed Sept. 21, 1973 now abandoned.

BACKGROUND OF THE INVENTION

The compounds employed in the method of the invention can be prepared by methods analogous to those described by Pollak et al., Tetrahedron 22, 2073 (1966), Miller and Rose, J. Chem. Soc. 1963, 5642, Basu and Rose, J. Chem. Soc. 1963, 5660 (1963), and Bellasio et al., U.S. Pat. Nos. 3,915,968 and 4,016,162.

SUMMARY OF THE INVENTION

This invention is directed to a method which comprises administering to a mammal a bronchodilating amount of a substituted triazolopyridazine compound or a pharmacologically-acceptable salt thereof, or a composition containing such substituted triazolopyridazine compound or salt as the active bronchodilator ingredient therein; said substituted triazolopyridazine compound corresponding to the formula

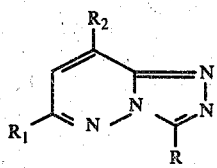

wherein R represents hydrogen, phenyl, loweralkyl or loweralkyl carbonylamido; $R_1$ represents morpholino (4-morpholinyl) or piperidino (1-piperidinyl) and $R_2$ represents hydrogen or loweralkyl, with the proviso that at least one of R and $R_2$ is a moiety other than hydrogen and with the further proviso that when R is phenyl, $R_1$ is morpholino and $R_2$ is loweralkyl. In the present specification and claims, "loweralkyl" is employed to refer to loweralkyl of one or two carbon atoms.

It has been found that the s-triazolo [4,3-b]-pyridazine compounds of the above formula and their pharmacologically-acceptable salts have potent bronchodilator properties. For the purpose of brevity, such compounds will be hereinafter referred to as "triazolopyridazines". The triazolopyridazine compounds have been found to block histamine-induced bronchial spasm. The compounds are also highly active in blocking the effects of serotonin and acetylcholine. The compounds have little or no significant detrimental pharmacological side effects at dosages consistent with good bronchodilator activity and have favorable toxicity.

Compounds of a structure somewhat similar to the compounds of the above formula have been found to have different properties. For example, 6-morpholino-s-triazolo [4,3-b]pyridazine, in which both R and $R_2$ are hydrogen, exhibits little or no significant bronchodilator activity in comparison to the compounds of the above formula in which either or both of R and $R_2$ are loweralkyl. 6-Methyl-3-(4-morpholinyl)-8-phenyl-s-triazolo[4,3-b]pyridazine, rather than blocking histamine-induced bronchoconstriction, has been found to potentiate bronchoconstriction. The compound 6-morpholino-3-phenyl-s-triazolo[4,3-b]pyridazine, although a potent bronchodilator with a high $LD_{50}$ (low toxicity), has been found to produce audiogenic convulsions in laboratory animals at relatively low dosages. For example, this compound produces audiogenic convulsions in mice at an $ED_{50}$ of 29 mg/kg, while 6-morpholino-3-phenyl-8-methyl-s-triazolo[4,3-b]pyridazine has an audiogenic convulsive $ED_{50}$ more than 12 times higher.

The triazolopyridazine compounds are crystalline solids which can be readily formulated in aqueous or alcoholic liquids. In general, the free base compounds are readily soluble in aqueous liquids, and the triazolopyridazine compounds are conveniently employed in either free base or salt form.

As employed herein, the phrase "pharmacologically-acceptable salt" refers to salts of the triazolopyridazines, the anions of which are relatively non-toxic and innocuous to mammals at dosages consistent with good bronchodilator activity so that side effects ascribable to the anions do not vitiate the beneficial effects of the triazolopyridazine compounds. Suitable pharmacologically-acceptable salts which can be employed in the method and composition of the invention can be prepared by conventional procedures.

In practicing the method, a bronchodilating amount of one or more substituted triazolopyridazine is administered internally to a mammal in need thereof by a route effective to bring the compound into contact with the bronchial and tracheal tissues of the mammal. Administration can be carried out either by a parenteral route, such as by intravenous, intraperitoneal, or intramuscular injection, or by introduction into the gastrointestinal tract via oral or rectal administration, for example, in order to bring about such contact via the blood stream, or by intratracheal administration, by inhalation of a solution in the form of a spray, for example.

The compounds wherein R is hydrogen or loweralkyl are generally more soluble in water than those wherein R is phenyl, and are a preferred group of compounds for use as bronchodilators. Another preferred group comprises compounds of the above formula wherein R is hydrogen or loweralkyl and $R_2$ is methyl, such compounds having superior activity.

The bronchodilating amount of the compound, that is, the amount of the substituted triazolopyridazine sufficient to inhibit or alleviate bronchial spasm depends on various factors such as the size, type and age of the animal to be treated, the particular triazolopyridazine or pharmacologically-acceptable salt employed, the route and frequency of administration, the severity of spasm (if any) and the causative agent involved, and the time of administration. In particular cases, the dosage to be administered can be ascertained by conventional range finding techniques, for example, by observing the bronchodilator activity produced at different dosage rates. Good results can be obtained when the compound is administered at dosage rates from about 1 to about 3, to about 10 to about 50 milligrams of substituted triazolopyridazine compound per kilogram of animal body weight. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are preferred and the active triazolopyridazine compound can be formulated in conventional timed release capsule or tablet formulations.

In practicing the method of the invention, the active ingredient is preferably incorporated in a composition comprising a pharmaceutical carrier and from about 5 to about 90 percent by weight of the substituted triazolopyridazine compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions, and can contain suitable excipients known to be useful in the preparation of the particular type of composition desired. The compounds may also be administered in conjunction with other active ingredients or other bronchodilator agents such as aminophylline or theophylline, for example, to utilize a combination of effects, synergistic action, combined bronchodilator and antibiotic activity, or in combination with agents having a somewhat different spectrum of bronchodilator activity.

DESCRIPTION OF PREFERRED EMBODIMENTS

The following examples illustrate the invention but are not to be construed as limiting the same.

EXAMPLE 1

This example illustrates the preparation of the compounds.

20 Grams of 3-hydrazino-4-methyl-6morpholinopyridazine are dispersed in 200 milliliters of 99 percent aqueous formic acid. The mixture is heated at the boiling temperature under reflux and then concentrated until an oily residue remains in the reaction vessel. The residue is taken up in aqueous sodium carbonate solution, and the aqueous mixture is extracted with chloroform. The chloroform extract is dried with anhydrous sodium sulfate, then evaporated under reduced pressure to obtain the 8-methyl-6-morpholino-s-triazolo[4,3-b]pyridazine product as the free base. The product is recrystallized twice from isopropanol and found to melt at 177°–178° C.

In substantially the same procedure, a mixture of 20 grams of 3-hydrazino-4-methyl-6-piperidinopyridazine in 100 milliliters formic acid is heated at reflux temperature for 3 hours and then evaporated to dryness. The residue is taken up in aqueous sodium carbonate and extracted with chloroform. After evaporation of the solvent, the 8-methyl-6-piperidino-s-triazolo[4,3-b]pyridazine product is recrystallized from ethyl acetate and found to melt at 118°–120° C. In a similar procedure, 3-methyl-6-morpholino-s-triazolo[4,3-b]pyridazine, melting at 165°–170° C., 3,8-dimethyl-6-morpholino-s-triazolo[4,3-b]pyridazine, melting at 212°–213° C., and 3,8-dimethyl-6-piperidino-s-triazolo[4,3-b]pyridazine, melting at 161°–163° C. are prepared.

The compounds wherein R is phenyl are prepared by reaction of the corresponding 3-hydrazino-4-alkyl-6-morpholinopyridazine with benzoyl chloride. For example, 3.5 grams of benzoyl chloride are added to a solution of 1.48 grams of 3-hydrazino-4-methyl-6-morpholinopyridazine and 1.8 grams of triethylamine, in 200 milliliters of dioxane and the mixture is refluxed for 3 hours. After evaporation of the solvent and washing with water, the 8-methyl-6-morpholino-3-phenyl-s-triazolo[4,3-b]pyridazine product is obtained, recrystallized from ethanol and found to melt at 271°–273° C. Compounds wherein R is phenyl can also be prepared by reacting a 3-chloro-4-loweralkyl-6-morpholinopyridazine with benzoyl hydrazide, preferably in equimolar proportions and at a temperature from the fusion point of the mixture to about 200° C. The latter reaction can be carried out without a solvent or in a solvent medium such as diethylene glycol methyl ether.

(The 3-loweralkyl carbonylamido compounds can be prepared by reacting the corresponding carbonyl chloride with the corresponding 3-amino-substituted-s-triazolo[4,3-b]pyridazine according to known procedures. The 3-amino-substituted-s-triazolo[4,3-b]pyridazine starting material is prepared by procedures analogous to those of Basu and Rose, J. Chem. Soc., 1963, 5660.)

EXAMPLE 2

Bronchodilator activity of representative triazolopyridazine compounds is examined in the Konzett-Rossler guinea pig preparation according to accepted procedures. See Konzett and Rossler, Arch. f. exp. Path. u. Pharmakol. 195: 71–74 (1940); and Rosenthale and Dervinis, Arch. int. Pharmacodyn, 172: 91–94 (1968). In this procedure, an anesthetized guinea pig is artificially respired with a fixed volume of air. This volume of air is selected to exceed the lung capacity, and the excess "overflow" volume is measured. Bronchoconstriction is produced by intravenous injection of a selected agonist (histamine, serotonin or acetylcholine) at five minute intervals at a dosage selected to produce 50 to 80 percent bronchoconstriction, as indicated by the resultant increase in "overflow" volume. Test compounds are evaluated by administering a test compound two minutes before the next agonist dose following three previous agonist doses resulting in relatively uniform ($\pm 10$ percent) bronchoconstriction. Bronchodilator activity, indicated by ability of a test compounds to block the agonist response, is expressed in terms of percent (%) block, calculated by dividing the agonist response(s) after the test drug by the average of the three agonist responses preceding the test compound, multiplying by 100 and subtracting this value from 100%. Aminophylline, a known bronchodilator, is also employed as a standard for comparison. In such procedure % block is determined for an intravenous dosage of 10 milligrams aminophylline per kilogram, then a test compound, then a repeat dosage of aminophylline. The results can be expressed as a percent of aminophylline, calculated by expressing the % blockade produced by the doses of aminophylline which precede and follow it.

Representative triazolopyridazines are employed as test compounds in this procedure at a dosage rate of 10 milligrams per kilogram. The results obtained are set out in the following Table:

TABLE I

| Compound No. | R | R₁ | R₂ | BRONCHODILATOR ACTIVITY | | | | | |
|---|---|---|---|---|---|---|---|---|---|
| | | | | HISTAMINE as agonist | | SEROTONIN as agonist | | ACETYLCHOLINE as agonist | |
| | | | | Average % Block. | Average % Amin. | Average % Block. | Average % Amin. | Average % Block. | Average % Amin. |
| 1 | $CH_3$ | morpholino | H | 75 | 96 | 68 | 112 | 66 | 124 |
| 2 | H | morpholino | $CH_3$ | 83 | 133 | 74 | 88 | 70 | 97 |
| 3[a] | H | piperidino | $CH_3$ | 87 | 234 | 82 | 103 | 84 | 147 |
| 4[a] | $CH_3CONH$ | piperidino | H | 53 | 72 | 49 | 87 | 68 | 131 |
| 5[a] | $CH_3CH_2CONH$ | piperidino | H | 55 | 61 | 67 | 85 | 59 | 117 |

[a]Compound 3 administered as the hydrochloride salt. Compounds 4 and 5 administered as hydrochloride salts against serotonin and acetylcholine.

EXAMPLE 3

The compounds 8-methyl-6-piperidino-s-triazolo[4,3-b]pyridazine and 8-methyl-6-morpholino-s-triazolo[4,3-b]pyridazine are evaluated in a procedure similar to that set out in Example 2. The test compounds are administered intraduodenally, rather than by intravenous injection. In these operations, the maximum response to a test compound is observed about 7 to 12 minutes after administration.

8-Methyl-6-piperidino-s-triazolo[4,3-b]pyridazine, administered as an aqueous solution of the hydrochloride salt, is found to produce 100 percent block of histamine when administered at a dosage of 10 milligrams per kilogram, and 36 percent block (average of three replications) at a dosage of 3 mg/kg. 8-Methyl-6-morpholino-s-triazolo[4,3-b]pyridazine, also administered as an aqueous solution, is found to produce a 53 percent block of histamine when administered at a dosage rate of 10 mg/kg. The results obtained with aminophylline in a similar procedure indicate the two test compounds to be somewhat more active than an equal dose of aminophylline.

EXAMPLE 4

The compounds of Example 2 are evaluated for twenty-four hour acute oral toxicity in mice. Compound 3 is found to have an acute oral $LD_{50}$ of 464 milligrams per kilogram, and the $LD_{50}$ of the remaining compounds is greater than 560 milligrams per kilogram.

The compounds 3-methyl-6-morpholino-s-triazolo[4,3-b]pyridazine and 8-methyl-6-morpholino-s-triazolo[4,3-b]pyridazine are evaluated in a battery of standard pharmacological tests to assess analgesic, barbiturate potentiation, anticoagulant and antidepressant activity. The results of such tests indicate a desirable low degree of undesired pharmacological effects.

EXAMPLE 5

In a procedure generally similar to that described in Example 2, the compounds 3-methyl-6-morpholino-s-triazolo[4,3-b]pyridazine; 8-methyl-6-morpholino-s-triazolo[4,3-b]pyridazine; 3,8-dimethyl-6-morpholino-s-triazolo[4,3-b]pyridazine; 3,8-dimethyl-6-piperidino-s-triazolo[4,3-b]pyridazine; and 8-methyl-6-piperidino-s-triazolo[4,3-b]pyridazine are evaluated as bronchodilators in the cat, using polyethylene glycol 200 in partial or complete replacement as a vehicle in certain cases to obtain a solution. Serotonin is employed as an agonist. The compounds are administered at rates of 5 or 10 milligrams per kilogram intravenously and found to give responses from 75 to 199 percent as great as are obtained with comparable dosages of aminophylline.

EXAMPLE 6

Audiogenic Convulsive Side Effects

Certain xanthine compounds, such as the known bronchodilator aminophylline, have central nervous system stimulant side effects which are difficult to detect in animal models which are satisfactory for evaluating other compounds. The interaction of sound with the convulsive threshold of drugs is a known phenomenon which can be used to evaluate such side effects. See, for example, Schlesinger et al., Life Science 4, 2345-2351 (1965), 7, 437-447 (1968) and 9 (I) 721-729 (1970) and Buckholtz, Pharmacol. Biochem. and Behavior 3, 65-68 (1975). In a procedure for pharmacological evaluation, the lowering of the convulsive threshold, or the lowering of the $LD_{50}$, by sound can be studied in mice.

In the test operations, mice are administered a test compound by intraperitoneal injection at various dosages, and the number of mice showing tonic convulsions and the number of fatalities occurring within 30 minutes is recorded. The $ED_{50}$ for tonic convulsions, and the 30 minute $LD_{50}$ are then determined. These operations are carried out in standard laboratory cages with mice that have become acclimated to the laboratory.

The surviving mice are then also exposed to sound about 30 minutes after dosing. The sound exposure is carried out by placing the mice in a sound insulated cage with a bell which emits 120 decibels of sound, and activating the bell for two minutes. The number of tonic convulsions and fatalities are then recorded to determine the $ED_{50}$ and $LD_{50}$ in the presence of the sound challenge.

In an experiment with aminophylline administered in 25% polyethylene glycol 200 and water, sound was found to lower the $LD_{50}$ by a factor of 7.25, from 313 mg/kg without sound to 43.2 with sound. A similar reduction in the toxic dose was observed for aminophylline in water, from an $LD_{50}$ of 390 mg/kg without sound to 44.3 mg/kg with sound. In a series of similar experiments, the ratio of the 30 minute $LD_{50}$ without sound to the sound-induced $LD_{50}$ for aminophylline, theophylline and caffeine was found to be greater than 3 for all three compounds, while strychnine exhibited no significant change in toxicity with sound.

Various triazolopyridazine compounds have been found to exhibit increased toxicity and lowered convulsive thresholds in such procedures, similar to aminophylline. Other triazolopyridazines which have bronchodilator activity exhibit much less toxic potential for audiogenic seizures. For example, the ratio of $LD_{50}$ without sound to $LD_{50}$ with sound for 6-morpholino-8-methyl-s-triazolo[4,3-b]pyridazine was found 1.3 while the ratio for the isomeric 8-morpholino-6-methyl-s-triazolo[4,3-b]pyridazine was found to be about 3.6.

Surprisingly, some triazolopyridazines have been found to exhibit a significant lowering of audiogenic convulsive threshold without an associated increase in sound-induced deaths, as indicated by a low $ED_{50}$ for audiogenic tonic convulsions in comparison to the $LD_{50}$ with sound. The compound 6-morpholino-3-phenyl-s-triazolo[4,3-b]pyridazine exhibits desirable bronchodilator activity; and its sound-induced $LD_{50}$ of 234 mg/kg is not greatly below its 30 minute $LD_{50}$ of 244 mg/kg. However, its $ED_{50}$ for audiogenic tonic convulsions is only 29 mg/kg. 6-Pyrrolidinyl-3-phenyl-s-triazolo[4,3-b]pyridazine has also been found to exhibit a similar reduced audiogenic convulsion $ED_{50}$.

In contrast, (a) 6-morpholino-8-methyl-s-triazolo[4,3-b]pyridazine; (b) 6-piperidino-8-methyl-s-triazolo[4,3-b]pyridazine; (c) 3,8-dimethyl-6-piperidino-s-triazolo[4,3-b]pyridazine; and (d) 6-morpholino-8-methyl-3-phenyl-s-triazolo[4,3-b]pyridazine did not exhibit such reductions in audiogenic convulsion $ED_{50}$'s. Compounds (b), (c) and (d) exhibited no sound-induced toxicity changes, and compound (a) exhibited a relatively minor increase in toxicity, from an $LD_{50}$ without sound of 317 mg/kg to an $LD_{50}$ with sound of 245 mg/kg, and an audiogenic convulsion $ED_{50}$ of 245 mg/kg. 3,8-Dimethyl-6-morpholino-s-triazolo[4,3-b]pyridazine was found to have an $LD_{50}$ of 185 mg/kg, an $LD_{50}$ with sound of 90 mg/kg and an audiogenic convulsion $ED_{50}$ of 83 mg/kg.

We claim:

1. A method useful for alleviating bronchial spasm in mammals, the method comprising administering internally to a mammal in need thereof a bronchodilating amount of a triazolopyridazine or a pharmacologically-acceptable salt thereof, the triazolopyridazine corresponding to the formula:

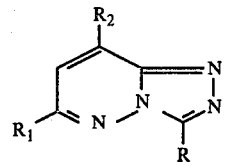

wherein R represents hydrogen, phenyl, loweralkyl or loweralkyl carbonylamido; $R_1$ represents morpholino or piperidino; and $R_2$ represents hydrogen or loweralkyl with the proviso that at least one of R and $R_2$ is a moiety other than hydrogen and with the further proviso that when R is phenyl, $R_1$ is morpholino and $R_2$ is loweralkyl.

2. The method of claim 1 wherein R is hydrogen and $R_2$ is methyl.

3. The method of claim 2 wherein $R_1$ is morpholino.

4. The method of claim 2 wherein $R_1$ is piperidino.

5. The method of claim 1 wherein the compound is administered orally at a dosage rate from about one to about 50 milligrams per kilogram of animal body weight.

6. The method of claim 1 wherein R is methyl.

7. The method of claim 1 wherein both R and $R_2$ are loweralkyl.